United States Patent [19]
Draeger et al.

[11] Patent Number: 4,551,427
[45] Date of Patent: Nov. 5, 1985

[54] PROCESS AND REAGENT FOR THE DETERMINATION OF BLOOD GLUCOSE IN HAEMOLYSED WHOLE BLOOD

[75] Inventors: Brigitte Draeger, Tutzing; Joachim Ziegenhorn, Starnberg, both of Fed. Rep. of Germany

[73] Assignee: Boehringer Mannheim GmbH, Mannheim, Fed. Rep. of Germany

[21] Appl. No.: 575,409

[22] Filed: Jan. 30, 1984

[30] Foreign Application Priority Data

Jan. 31, 1983 [DE] Fed. Rep. of Germany ....... 3303098

[51] Int. Cl.$^4$ .............................................. C12Q 1/54
[52] U.S. Cl. ........................................ 435/14; 436/67
[58] Field of Search ............................ 435/14; 436/67

[56] References Cited
U.S. PATENT DOCUMENTS 4,416,982 11/1983 Tsuda et al. ........................... 435/14

OTHER PUBLICATIONS
Chemical Abstracts Index Guide, (1982), p. 1285G.

Primary Examiner—Sam Rosen
Attorney, Agent, or Firm—Felfe & Lynch

[57] ABSTRACT

A reagent and improved process for the determination of D-glucose in body fluids by reaction with ATP in the presence of hexokinase, glucose-6-phosphate dehydrogenase, NADP, $Mg^{++}$ ions and buffer and measurement of the NADPH formed. The improved process requires, before reaction with ATP, the mixing of the whole blood with a reagent which is composed of 0.01 to 0.5% weight/volume of an alkyl sulphate or sulphonate or of an alkyl-aryl sulphonate wherein the alkyl moiety is $C_8$ to $C_{32}$ and optionally contains one or more hydroxylalkylamino radicals as substituents and/or is interrupted by one or more ether oxygen atoms and the alkyl-aryl radicals having $C_8$ to $C_{18}$ alkyls and optionally a preserving agent.

17 Claims, No Drawings

PROCESS AND REAGENT FOR THE DETERMINATION OF BLOOD GLUCOSE IN HAEMOLYSED WHOLE BLOOD

The present invention is concerned with a process and a reagent for the determination of blood glucose in haemolysed whole blood by the hexokinase/glucose-6-phosphate dehydrogenase process.

The determination of blood glucose is one of the most frequent clinical-chemical analyses carried out in the laboratory. It is carried out in large numbers not only routinely but also for emergency analyses.

Especially for the control of blood glucose by diabetics, for the determination of glucose there are required small sample volumes (sampling of capillary blood from the finger tips), stability of the samples for a comparatively long period of time (sending of the samples) and a simple carrying out of the determination with high precision and correctness.

For the determination of the D-glucose concentration in blood fluids, the hexokinase/glucose-6-phosphate dehydrogenase method is internationally regarded as being a reference method. In the case of this method, D-glucose is converted with ATP in the presence of hexokinase (HK) into glucose-6-phosphate and the latter reacted with glucose-6-phosphate dehydrogenase (G6PDH) and NADP to give gluconate-6-phosphate and $NADPH + H^+$.

The sample material normally used is deproteinised whole blood or serum or plasma. This necessitates a time- and labour-consuming pretreatment of the samples.

It would be considerably simpler to dissolve the cells (erythrocytes) present in the blood by suitable additives and to determine the glucose in the homogeneous solution so obtained.

However, it is a prerequisite for a correct glucose determination in the haemolysate that the enzymes of glycolysis and of the pentose phosphate cycle reacting the glucose present in human erythrocytes, which enzymes are liberated by the haemolysis, are inhibited.

The literature describes various inhibitors for the erythrocyte enzymes (for example fluorides, N-alkylmaleimides, haloacetates and the like), the disadvantage of which is, however, that they do not completely inhibit glycolysis in the haemolysate or that the stability of the inhibitors in the solution is insufficient (for example in the case of maleimides and haloacetates).

Thus, for example, an important prerequisite for a determination of the glucose in the haemolysate with the help of the hexokinase method as detection system is the complete inhibition of the gluconate-6-phosphate dehydrogenase contained in the erythrocytes since this enzyme further reacts gluconate-6-phosphate, which is formed by the glucose detection reaction, with the formation of NADPH, which simulates too high glucose values.

A recently described haemolysis agent for the determination of glucose in blood consists of a buffered EDTA-detergent solution. It is admittedly stable and inhibits the breakdown of glucose in the haemolysate but does not sufficiently inhibit the gluconate-6-phosphate dehydrogenase, which results in a creep reaction in the test system.

A haemolysis agent consisting of maleimide and digitonin does not display any influencing of the glucose determination according to the hexokinase method but, nevertheless, it displays two disadvantages: limited stability of the haemolysis agent and turbidity of the haemolysate when stored at ambient temperature for more than 3 days.

Therefore, it is an object of the present invention to provide a process for carrying out the determination of blood glucose in haemolysed blood according to the hexokinase/glucose-6-phosphate dehydrogenase method which does not display the disadvantages of the known methods and, in particular, completely inhibits the enzymes of glycolysis and of the pentose phosphate cycle liberated from the erythrocytes, provides a stable haemolysis agent and does not bring about either a turbidity of the haemolysate in the case of storage or an instability of the glucose in the haemolysate.

Thus, according to the present invention, there is provided a process for the determination of D-glucose in body fluids by reaction with ATP in the presence of hexokinase, glucose-6-phosphate dehydrogenase, NADP, $Mg^{++}$ ions and buffer and measurement of the NADPH formed, wherein whole blood is mixed with 0.01 to 0.5% weight/volume of an alkyl sulphate or sulphonate or alkyl-aryl sulphonate, whereby the alkyl radicals can contain 8 to 32 carbon atoms and can contain one or more hydroxyalkylamino radicals as substituents and/or can be interrupted by one or more ether oxygen atoms and the alkyl-aryl radicals can contain 8 to 18 carbon atoms in the alkyl moiety, and optionally with a preserving agent, the said further reagents then being added directly.

In carrying out the process according to the present invention, as a rule, a small amount of whole blood is added to a solution which contains the given concentration of sulphate or sulphonate, for example in the ratio of blood to haemolysis solution of 1 to 4:100.

Surprisingly, we have found that the said alkyl sulphates, alkyl sulphonates and alkyl-aryl sulphonates bring about an extremely rapid haemolysis of the erythrocytes in the blood and the enzymes thereby liberated are so completely inhibited that they do not bring about any disturbance of the HK/G6PDH method but, on the other hand, also no disturbance of this method itself or inhibition of the enzymes employed is brought about.

The process according to the present invention gives a stable measurement signal (end point determination) which is not achieved in the case of the known haemolysis reagent consisting of EDTA and polyoxyethylene-10-alkylphenol ether. This can be seen from the Figure of the accompanying drawings which shows the measured extinction differences in dependence upon the time for the process according to the present invention, as well as with the use of the known, above-described haemolysis reagent. It can be seen that in the case of the process according to the present invention, the measurement value is stable, whereas in the case of the known haemolysis agent, it continuously increases further and thus leads to an intolerable error in the determination.

It was not to have been foreseen that, with the process according to the present invention, the initially described problem can be solved since it is known from Life Sciences, 31, 463–470/1982 that, for example, dodecyl sulphate competitively inhibits G6PDH towards glucose-6-phosphate. Therefore, it was to have been expected that the HK/G6PDH method could not be carried out in the presence of the alkyl sulphates, sulphonates and/or alkyl-aryl sulphonates employed according to the present invention.

In the case of the sulphates and sulphonates used according to the present invention, the length of the alkyl radicals, when they are not interrupted by ether oxygen atoms, is preferably between 10 and 18 carbon atoms and when they contain an ether bridge is preferably between 20 and 28 carbon atoms. As aryl radical, the phenyl radical is preferred. By hydroxyalkylamino radicals, there are preferred the mono-, di- and triethanolamine groups but the alkanol residue in the amine group can, however, contain 1 to 4 carbon atoms.

Typical examples for sulphates and sulphonates suitable according to the present invention include decyl sulphate, undecane-1-sulphonate, tetradecyl sulphate, lauryl myristyl ether sulphate, monoethanolamine lauryl sulphate, triethanolamine lauryl sulphate, dodecylphenyl sulphonate and tetrapropylenebenzene sulphonate.

The organic sulphates and sulphonates used according to the present invention can be employed in pure form. However, mixtures can also be used, such as are commercially available. The mixture which is commercially available as dodecyl sulphate but which, besides dodecyl sulphate itself, can also contain a certain amount of sulphates having longer and shorter alkyl chains, has proved to be especially suitable.

The organic sulphates and sulphonates used according to the present invention are preferably employed in the form of their sodium, lithium and ammonium salts. However, salts of other non-disturbing cations can also be used.

The concentration of the sulphate or sulphonate used according to the present invention must be within the range of from 0.01 to 0.5% by weight per unit volume of the haemolysate. In the case of a lower concentration, the inhibition of the disturbing enzymes is not complete and in the case of higher additions the enzymes required for the determination are also inhibited.

As a rule, use is made of an aqueous solution with the stated content of sulphate or sulphonate to which are added 10 to 30 μl. and preferably 15 to 25 μl. of whole blood per ml. of reagent solution.

Furthermore, there is preferably also added a preserving agent which serves not only for the preservation of the haemolysis agent but also for the preservation of the haemolysate itself and thus makes it possible to interrupt the process, after preparation of the haemolysate, for a comparatively long period of time without the analysis results hereby being influenced.

Preferred preserving agents include the alkali metal azides, especially sodium azide. However, other conventional preserving agents, such as thiocid, chlorhexidine and imidazoline-urea, also prove to be suitable, by which it is to be understood that they do not disturb the test. The mentioned preserving agents are thereby used in the usual concentrations, for example in the case of the azides of about 0.1 mg./ml., in the case of thiocid of about 0.2 mg./ml., in the case of chlorhexidine of about 0.25 mg./ml. and in the case of imidazoline-urea of about 10 mg./ml.

The present invention also provides a reagent for carrying out the process according to the present invention, wherein it contains alkyl sulphate or sulphonate or alkyl-aryl sulphonate, whereby the alkyl radicals can contain 8 to 32 carbon atoms and can contain one or more hydroxyalkylamino radicals as substituents and/or can be interrupted by one or more ether oxygen atoms and the alkyl-aryl radicals can contain 8 to 18 carbon atoms in the alkyl moiety, and a preserving agent and optionally a buffer of pH 6 to 9.

The sulphate or sulphonate is preferably present in the form of the sodium, lithium or ammonium salt.

As preserving agents, those mentioned above are preferred and especially preferred are the alkali metal azides, particularly sodium azide.

The ratio of sulphate or sulphonate to preserving agent depends essentially upon the nature of the preserving agent which, in turn, determines the concentration in the haemolysis reagent solution ready to use. The amount of the preserving agent is normally such that, in the haemolysis reagent solution ready for use, concentrations are obtained which are normally recommended for the preserving agent. Usual values for the mentioned preserving agents are given above. For the composition dodecyl sulphate/sodium azide, there follows therefrom a weight ratio of 0.3 to 5 parts by weight of dodecyl sulphate per part by weight of sodium azide.

The process according to the present invention gives, in comparison with the reference method carried out in deproteinised blood, an excellent agreement, as the following Table shows:

| reference method (sample: deproteinised blood) | haemolysis method according to the present invention |
|---|---|
| 155.3 mg./dl. | 155.2 mg./dl. |
| 151.3 mg./dl. | 150.6 mg./dl. |
| 79.3 mg./dl. | 77.6 mg./dl. |
| 105.4 mg./dl. | 107.5 mg./dl. |

The process and reagent according to the present invention fulfil all the requirements which must be demanded of a practicable haemolysate method, namely:

(a) small blood volumes (venous blood, capillary blood): 20 μl./1 ml. of haemolysis reagent or 10 μl./0.5 ml. of haemolysis reagent;

(b) no test disturbance in the hexokinase method: no creep reaction, good agreement with the reference method (deproteinised blood as sample and the hexokinase method for the detection of glucose);

(c) very good stability of the glucose in the haemolysate (30 days at ambient temperature), i.e. a very good inhibition of the glucose-reacting enzymes present in the haemolysate;

(d) unlimited storage stability of the haemolysis reagent;

(e) simple preparation of the reagent; dissolving of the alkyl sulphate or sulphonate, for example of dodecyl sulphate, in water and addition of the preserving agent; and (f) very good haemolysing properties, haemolysis taking place within a few seconds; no precipitates are formed in the haemolysate even over comparatively long periods of time (30 days at ambient temperature).

The following Examples are given for the purpose of illustrating the present invention:

EXAMPLE 1

(A) Preparation of the haemolysis reagent 1.8 g. Ammonium dodecyl sulphate and 1 g. sodium azide are dissolved in 1 liter of water.

(B) Carrying out of the test (a) Preparation of haemolysate

20 μl. blood are mixed with 1 ml. of the haemolysis reagent. For rapid haemolysis, the mixture is briefly shaken.

(b) Measurement of glucose in the haemolysate. End point determination (manual carrying out of the test)

500 μl. of the haemolysate are mixed with 2 ml. of the following reagent: 35 mmol/liter phosphate buffer (pH 7.7); 2 mmol magnesium sulphate; 0.65 mmol NADP; and 0.65 mmol ATP.

The extinction of the mixture of haemolysate and reagent is measured at a wavelength of 365 nm. The reaction is started by the addition of 20 μl. enzyme solution, which contains 125 KU/liter glucose-6-phosphate dehydrogenase and 110 KU/liter hexokinase. After 5 minutes, the reaction is finished. From the extinction difference before and after the addition of the enzyme solution, there can be calculated the glucose concentration of the blood:

mg./dl glucose = 1323.4 × $\Delta E_{365}$ nm.

EXAMPLE 2

Kinetic determination (automatic analyser: Eppendorf ACP 5040)

Reagent for the glucose determination: 70 mmol/liter phosphate buffer (pH 7.7); 4 mmol/liter magnesium sulphate; 1.3 mmol/liter NADP; 5 mmol/liter ATP. Enzyme solution: 12.5 KU G6PDH; 11 KU hexokinase. Carrying out of the test:

250 μl. of reagent are mixed with 50 μl. of a haemolysate obtained according to Example 1 (B) and the reaction is started with 25 μl. of the enzyme solution described in Example 1. 30 seconds after the start of the reaction, the kinetics are measured for 6.7 seconds.

Calibration takes place by means of a glucose standard. The values obtained are expressed in mg./dl. of glucose.

EXAMPLES 3 TO 13

The procedure is as described in Example 1 but, instead of dodecyl sulphate, there are used the sulphates and sulphonates given in the following Table. The Table also shows the concentrations used in the haemolysis reagent, these statements of concentration referring to the commercial products, as well as the change of extinction which takes place over 30 minutes and, finally, also the amount of glucose found, expressed as a percentage of the glucose initially present.

| Example | sulphate or sulphonate | concentration of haemolysis agent | extinction change 5 to 35 minutes after start of reaction (creep reaction) | glucose found |
|---|---|---|---|---|
| 3 | decyl sulphate | 0.25% | 4 mE[1] | 96% |
| 4 | undecane-1-sulphonate | 0.25% | −2 mE[1] | 96% |
| 5 | tetradecyl sulphate* | 0.25% | 2 mE[1] | 100% |
| 6 | Texapon F (mixture of fatty alcohol sulphates and alkyl aryl sulphonates; 45%) | 0.2% | 2 mE[1] | 99% |
| 7 | Merpisap DP 82 (tetrapropylene-benzene-sulphonate; 83%) | 0.1% | 2 mE[1] | 103% |
| 8 | Reworyl NKS 50 (dodecylphenyl-sulphonate; 50%) | 0.15% | 1 mE[1] | 100% |
| 9 | Hostapur AT (alkane sulphonate) | 0.15% | 2 mE[1] | 100% |
| 10 | Texapon K 14 S Spezial (lauryl myristyl ether sulphate; 30%) | 1% | 1 mE[2] | 99% |
| 11 | Texapon MLS (mono-ethanolamine lauryl sulphate; 28%) | 0.05% | 2 mE[2] | 98% |
| 12 | Texapon ASV (mixture of special alkyl sulphates; 28%) | 0.5% | −2 mE[2] | 106% |
| 13 | Texapon TH (tri-ethanolamine lauryl sulphate; 47–48%) | 0.5% | −3 mE[2] | 97% |

Statements of the composition and concentration are taken from Emulsifiers and Detergents, International Edition, 1981.

[1] 20 μl. blood/ml. haemolysis reagent, measurement at 366 nm.
[2] 10 μl. blood/ml. haemolysis reagent, measurement at 334 nm.
*In order to bring the substance into solution, 0.5% isooctyl phenyl ether was added to the reagent.

We claim:

1. In a process for the determination of D-glucose in a blood sample by reaction with ATP in the presence of hexokinase, glucose-6-phosphate dehydrogenase, NADP, $Mg^{++}$ ions and buffer and measurement of the NADPH formed, the improvement comprising, before reaction with ATP, the step of mixing the blood sample with 0.01 to 0.5% weight/volume of an alkyl sulphate, an alkyl sulphonate or an alkyl-aryl sulphonate, wherein the alkyl radicals contain 8 to 32 carbon atoms and are unsubstituted or substituted by one or more hydroxyalkylamino radicals as substituents and are uninterrupted or interrupted by one or more ether-oxygen atoms and the alkyl-aryl radicals contain 8 to 18 carbon atoms in the alkyl moiety.

2. Process according to claim 1, wherein dodecyl sulphate is used.

3. Process of claim 1 wherein a preserving agent is used along with the sulphate or sulphonate.

4. Process according to claim 3 wherein an alkali metal azide, thiocid, chlorhexidine or imidazoline-urea is used as the preserving agent.

5. Process of claim 1 wherein an alkyl sulphate is used.

6. Process of claim 1 wherein an alkyl sulphonate is used.

7. Process of claim 1 wherein an alkyl-aryl sulphonate is used.

8. Process of claim 1 wherein an alkyl-phenyl sulphonate is used.

9. A reagent for use in an improved method for determination of D-glucose in a blood sample of the type wherein the blood sample is reacted with ATP in the presence hexokinase, glucose-6-phosphate dehydrogenase, NADP, $Mg^{++}$ ions and buffer, whereafter the NADPH formed is measured, the improvement being in reacting the blood sample with said reagent before reaction with ATP; said reagent comprising, effective amounts of alkyl sulphate or sulphonate or alkyl-aryl sulphonate, wherein the alkyl radicals contain 8 to 32 carbon atoms and are unsubstituted or substituted by one or more hydroxyalkylamino radicals as substituents, and are uninterrupted or interrupted by one or more ether-oxygen atoms and the alkyl-aryl radicals contain 8 to 18 carbon atoms in the alkyl moiety, and a preserving reagent selected from the group consisting of alkali metal azides, thiocid, chlorhexidine and imidazoline-urea.

10. Reagent of claim 9 consisting of dodecyl sulphate and said preserving agent.

11. Reagent according to claim 10, wherein it contains dodecyl sulphate and sodium azide in a weight ratio of 0.3 to 5:1.

12. Reagent of claim 9 wherein an alkyl sulphate is used.

13. Reagent of claim 9 wherein an alkyl sulphonate is used.

14. Reagent of claim 9 wherein an alkyl-aryl sulphonate is used.

15. Reagent of claim 9 wherein an alkyl-aryl sulphonate is used.

16. Reagent of claim 9 wherein an alkyl-phenyl sulphonate is used.

17. Test kit for determination of D-glucose in body fluids comprising a first reagent composed of alkyl sulphate, alkyl sulphonate or alkyl-aryl sulphonate wherein the alkyl radicals contain 8 to 32 carbon atoms and are unsubstituted or substituted one or more times by hydroalkylamino radicals; and are uninterrupted or interrupted one or more times by ether-oxygen atoms; and the alkyl-aryl radicals contain 8 to 18 carbon atoms in the alkyl moiety; and a second reagent comprising ATP, hexokinase, glucose-6-phosphate dehydrogenase, NADP, $Mg^{++}$ ion source and buffer, all in effective amounts for determination of D-glucose in body fluids by formation and measurement of NADPH.

* * * * *